United States Patent [19]
Wallin

[11] Patent Number: 5,517,314
[45] Date of Patent: May 14, 1996

[54] OPTICAL ANALYSING EQUIPMENT FOR DETERMINING PARAMETERS OF GASEOUS SUBSTANCES FLOWING THROUGH A DUCT

[75] Inventor: Svante Wallin, Bjärred, Sweden

[73] Assignee: Opsis AB, Furulund, Sweden

[21] Appl. No.: 281,863

[22] Filed: Jul. 28, 1994

Related U.S. Application Data

[63] Continuation of Ser. No. 986,075, Dec. 4, 1992, abandoned.

[30] Foreign Application Priority Data

Dec. 4, 1991 [SE] Sweden ................................ 9103624
Apr. 3, 1992 [SE] Sweden ................................ 9201052

[51] Int. Cl.$^6$ ........................................ G01N 21/00
[52] U.S. Cl. .................... 356/437; 356/438; 250/345; 250/252.1
[58] Field of Search ........................ 356/432–440, 356/315, 323, 325, 308, 244, 246; 359/888; 250/573, 575, 576, 236, 252.1 A, 343, 345; 73/1 R, 1 G

[56] References Cited

U.S. PATENT DOCUMENTS

| | | | |
|---|---|---|---|
| 3,809,913 | 5/1974 | Prellwitz | 356/439 |
| 3,838,925 | 10/1974 | Marks | 356/435 |
| 3,872,315 | 3/1975 | Boll | 356/439 |
| 3,885,162 | 5/1975 | Geertz | 356/439 |
| 4,023,909 | 5/1977 | Ross | 356/434 |
| 4,231,663 | 11/1980 | Phillippi | 356/432 |
| 4,381,153 | 4/1983 | Bohl et al. | 356/437 |
| 4,445,359 | 5/1984 | Smith | 356/437 |
| 4,544,273 | 10/1985 | Berndt | 356/438 |
| 4,583,859 | 4/1986 | Hall, II | 356/438 |
| 4,687,337 | 8/1987 | Stewart et al. | 356/437 |
| 4,835,393 | 5/1989 | Krauss | 356/438 |
| 5,218,428 | 6/1993 | Hoult | 356/440 |

FOREIGN PATENT DOCUMENTS

| | | |
|---|---|---|
| 0159157 | 10/1985 | European Pat. Off. . |
| 0417884A2 | 3/1991 | European Pat. Off. . |
| 453017 | 1/1988 | Sweden . |
| WO84/04392 | 5/1983 | WIPO . |
| WO86/07455 | 12/1986 | WIPO . |

OTHER PUBLICATIONS

Patent Abstract of Japan, vol. 7, No. 64 (P–183), Abstract of JP 57–207848, published 20th Dec. 1982, Horiba Seisakusho K.K.

Primary Examiner—Hoa Q. Pham

[57] ABSTRACT

Optical analysing equipment includes a light source, a light receiver and an optical arrangement for producing a measuring beam and a calibrating beam from the light of the light source. A calibrating channel and a measuring channel extend form the light source to the light receiver. The light source and the light receiver can be arranged on opposite sides of the duct. In this case, the calibrating channel and the measuring channel include two tubes extending in parallel across the duct between the light source and the light receiver. The light source and the light receiver can alternatively be arranged on the same side of the duct. In this case, the measuring channel extends partially into the duct. The calibrating channel may then extend into the duct or be positioned entirely outside the duck. By light control means, the light receiver receives either the measuring beam or the calibrating beam.

43 Claims, 3 Drawing Sheets

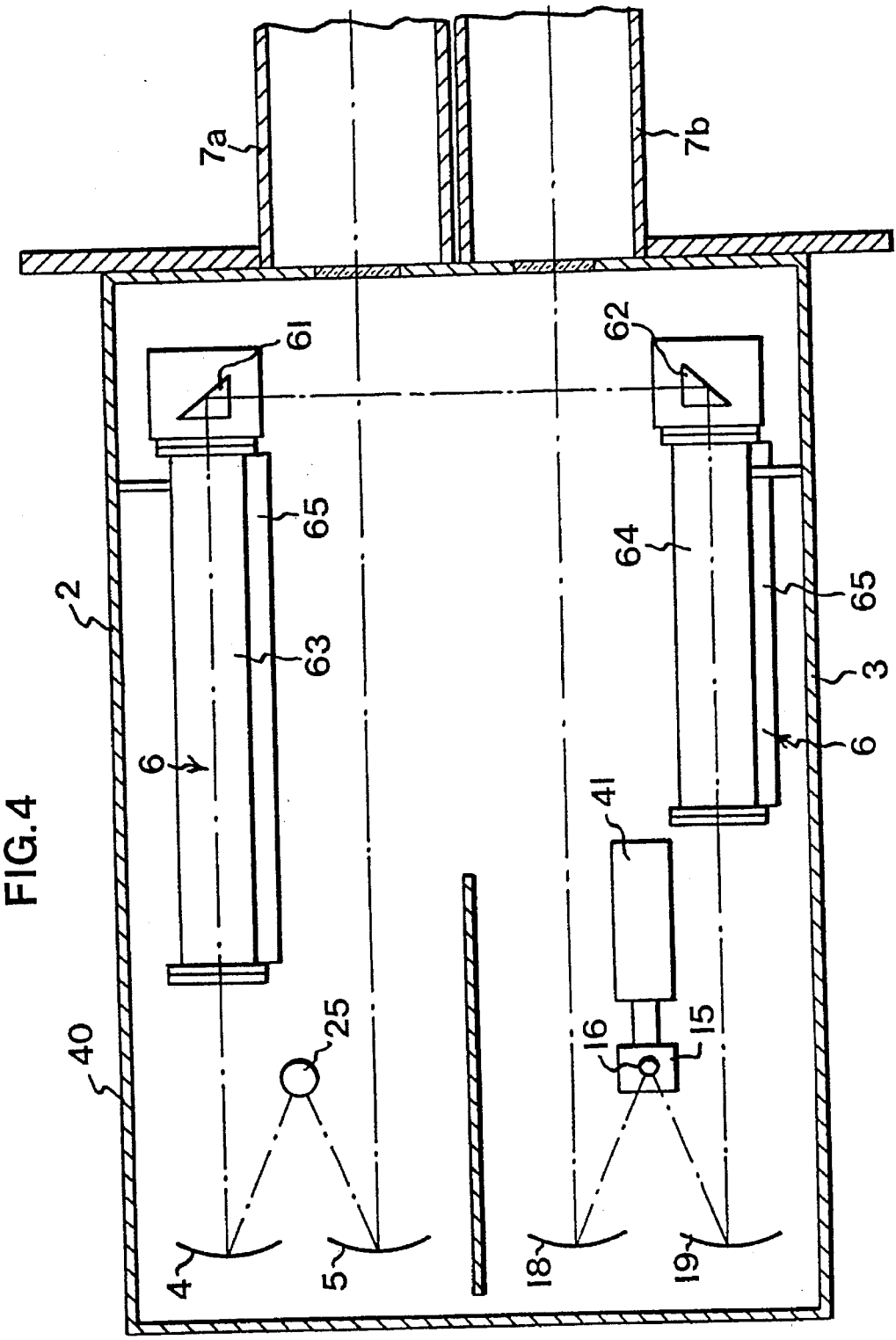

OPTICAL ANALYSING EQUIPMENT FOR DETERMINING PARAMETERS OF GASEOUS SUBSTANCES FLOWING THROUGH A DUCT

This application is a continuation, of application Ser. No. 07/986,075, filed on Dec. 4, 1992, now abandoned.

TECHNICAL FIELD

The present invention relates to an optical analysing equipment for determining parameters especially the concentration, of gaseous substances flowing through a duct.

BACKGROUND ART

SE 453,017 discloses an optical analysing equipment which may be used in e.g. a chimney for determining different parameters of gaseous substances, such as $SO_2$, $NO_2$ and NO, in the gas volume flowing through the chimney. The parameters are determined by emitting light from a light transmitter On one side of the chimney to the gas volume, by receiving the light, which is transmitted through the gas volume, by a light receiver on the other side of the chimney, and by analysing the received light by means of the actual analysing equipment which may be positioned at a distance from the chimney.

Before mounting the light transmitter and the light receiver in the chimney, the analysing equipment is calibrated. It should then be calibrated at regular intervals to compensate for, inter alia, the ageing of the components. In order to carry out the calibration, it is today necessary to dismount the light transmitter and the light receiver from the chimney and instead mount them on a container to which different gases of a known composition and concentration may be supplied. This is a time-consuming method of carrying out the calibration, which also demands a great deal of work and which is not suitable to use if frequent calibration of the equipment is desirable.

U.S. Pat. No. 4,381,153 discloses an opacity monitor which permits calibration on site. The opacity monitor comprises a light source mounted on one side of a duct, and a detector mounted on the opposite side of the duct. The light source and the detector are rotatable by motor means between a first position aligned with each other along an open light path defined across the duct, and a second position aligned with each other on opposite sides of a calibration tube extending across the duct. Shutters rotate with the light source and the detector, and the shutters are aligned with the calibration tube when the light source and the detector are aligned with the open light path, and vice versa. By rotating the light source and the detector to the second position, calibration can thus be carried out when the device is mounted at the duct.

However, it is a well-known fact that movable parts often cause reliability and maintenance problems. Moreover, problems may arise when using the device according to U.S. Pat. No. 4,381,153 in very large chimneys in which it may be difficult to mount the calibration tube.

One object of the invention therefore is to provide an optical analysing equipment which permits calibration on site, with as few movable parts as possible.

A further object of the invention is to provide an optical analysing equipment which is intended for ducts having an extremely great diameter and which permits calibration on site.

SUMMARY OF THE INVENTION

According to one aspect of the invention, an optical analysing equipment for determining parameters, especially the concentration, of gaseous substances flowing through a duct has been provided. The apparatus comprises a fixed light source which is arranged on one side of the duet, a fixed optical arrangement which is adapted to simultaneously produce, from the light of the light source, a first and a second light beam, a light receiver arranged opposite the light source, calibrating channel means extending through the duct and comprising at least one calibrating cell into which a calibrating medium is introducible, the fixed optical arrangement being adapted to direct the first beam through the calibrating channel means to the light receiver, measuring channel means extending through the duct and arranged to provide a measuring path of a predetermined length in the duct, the fixed optical arrangement being adapted to direct the second beam through the measuring channel means to the light receiver, and light control means, by which the light receiver can be caused to selectively receive the first or the second light beam.

Since the fixed optical arrangement divides the light from the light source into two beams, a measuring beam and a calibrating beam, no rotation of the light source is required, but this may be fixedly mounted. By a light control means, the light receiver is caused to receive either the measuring beam or the calibrating beam. Furthermore the light control means may comprise shielding means, and the light receiver may be fixedly mounted.

According to a further aspect of the invention, an optical analysing equipment for determining parameters, especially the concentration, of gaseous substances flowing through a duct, has been provided. The apparatus comprises a light source which is arranged on one side of the duet, an optical arrangement which is adapted to produce, from the light of the light source, a first and a second light beam, a light receiver which is arranged on essentially the same side of the duct as the light source, calibrating channel means which comprises at least one calibrating cell into which a calibrating medium is introducible, the optical arrangement being adapted to direct the first light beam through the calibrating channel means, measuring channel means which are arranged to provide a measuring channel which extends a distance into the duct and then back to the light receiver and which has an open portion for providing a measuring path of a predetermined length in the duct, the optical arrangement being adapted to direct the second light beam through the measuring channel means, and light control means by which the light receiver can be caused to selectively receive the first or the second light beam.

This embodiment of the invention is especially suitable for use in ducts having a great diameter, in which it is difficult to mount a calibrating tube across the duct. According to this embodiment, the light receiver and the light transmitter are arranged on the same side of the duct by measuring channel means extending a distance to the duct. The calibrating channel can be arranged partly in parallel with the measuring channel and extend into the channel, or be placed outside the channel.

BRIEF DESCRIPTION OF THE DRAWINGS

FIG. 4 is a partial top plan view of a third embodiment of the invention.

DETAILED DESCRIPTION

Figure 1:
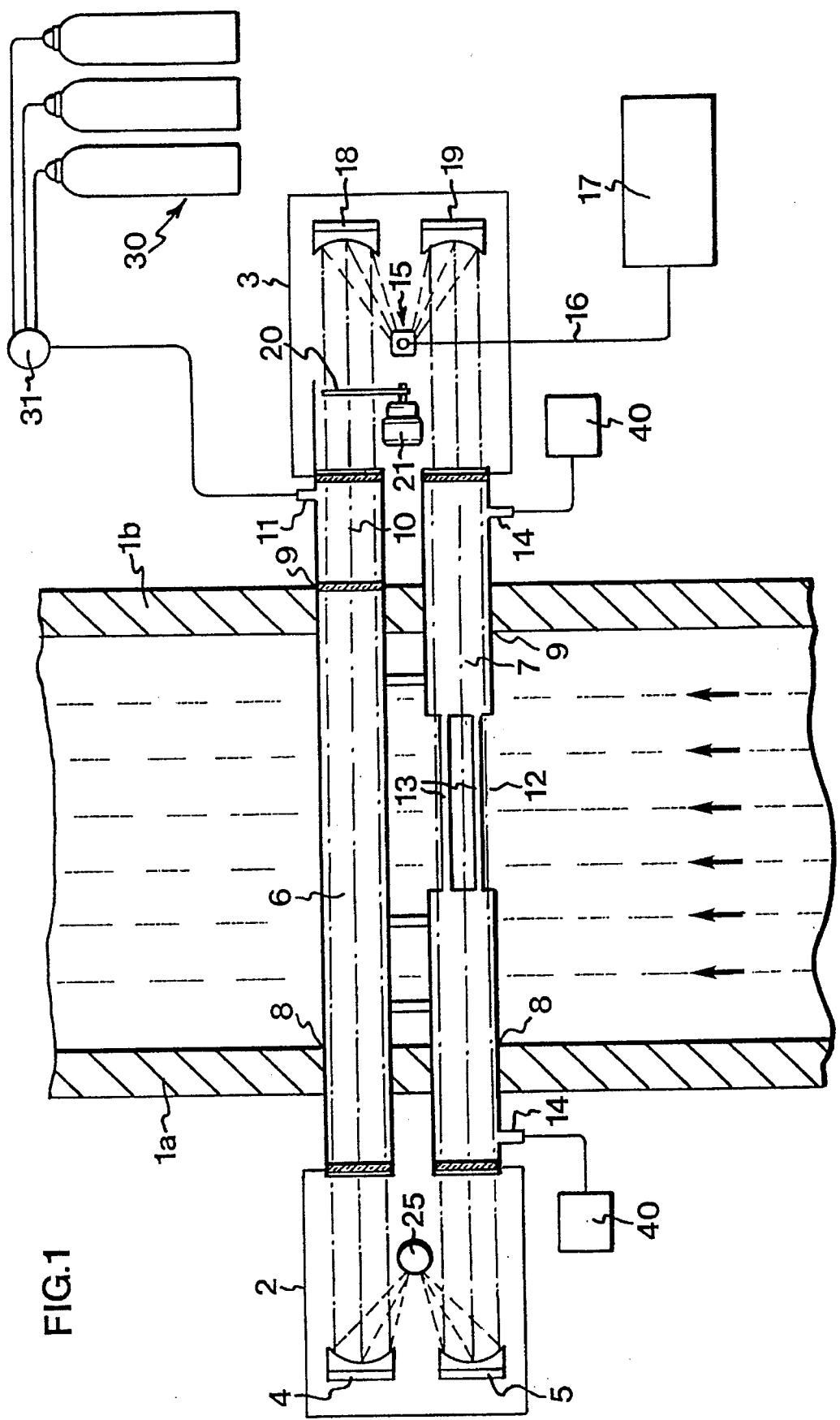
FIG. 1 illustrates a first embodiment of an optical analysing equipment.

FIG. 1 illustrates a first embodiment of the equipment according to the invention mounted in a chimney with walls 1a and 1b. The equipment comprises a transmitter unit 2 which is mounted outside one wall 1a of the chimney, and a receiver unit 3 which is mounted opposite the transmitter unit 2 outside the other wall 1b of the chimney. The transmitter unit 2 comprises a lamp 25 and two parabolic mirrors 4, 5 which are arranged to reflect the light from the lamp in two parallel light beams.

The transmitter unit 2 is connected to the receiver unit 3 via a calibrating unit and a measuring unit comprising two parallel tubes 6, 7 which extend through openings 8 and 9 in the walls 1a and 1b, respectively, of the chimney and which preferably are Joined together. One tube 6, which is a calibrating tube, it completely closed. The gases in the chimney can thus not penetrate into the calibrating tube, and the light passing through the calibrating tube therefore is quite unaffected by the gases. In the part of the calibrating tube 6 which is located between the chimney wall 1b and the receiver unit 3 is a calibrating cell 10 which has at least one inlet 11 to which different containers 30 with gaseous substances having a known concentration can be connected via a valve arrangement 31. Alternatively, the calibrating cell 10 can be arranged in the part of the calibrating tube 6 which is located inside the chimney. This positioning of the calibrating cell 10 has the advantage that the calibration is carried out at a temperature which is the same as that of the gases in the chimney.

The other tube 7, which is a measuring tube, has an open portion 12 through which the gases in the chimney can flow freely. This open portion 12 is in the simplest way formed by the milling of openings in a closed tube in such a manner that Just a few rods 13, which connect the closed parts of the measuring tube 7, remain. The open portion 12 forms for the equipment a well-defined measuring path which, for example, may have a length in the range 0.5–2 m. In each end of the measuring tube 7 there are also inlets 14 for purge air which are connected to means 40 for supplying purge air.

The tubes 6, 7 are made of stainless steel. The total length may vary up to, for example, 7 m. The inner diameter is e.g. 85 mm. Only one end of the tubes is preferably attached to the wall of the chimney. The other end is attached to a sliding arrangement (not shown) which allows linear expansion of the tubes as the temperature varies.

The receiver unit 3 comprises a light receiver 15 comprising an optical fibre 16 which is connected to an analysing unit 17. The receiver unit 3 further comprises two parabolic mirrors 18 and 19 which are arranged to reflect light from the calibrating tube 6 and the measuring tube 7, respectively, to the light receiver 15. These mirrors are, like the other mirrors, formed with a layer of aluminium covered by a thin layer of $MgF_2$.

The receiver unit 3 also accommodates a shielding means 20 which is controlled by a motor 21 to take one of two positions. In one position (shown in the Figure) the shielding means 20 prevents light from the calibrating tube 6 from reaching the light receiver 15, and in the other position it prevents light from the measuring tube 7 from reaching the light receiver 15.

Moreover, the equipment comprises a computer (not shown) which is adapted to control, inter alia, the motor 21 and the valve arrangement 31 for carrying out automatic calibration.

The function of the equipment will be described below.

For the measuring operation, the shielding means 20 is placed by the motor 21 in the position shown in the Figure. Light is emitted from the lamp 25 to the parabolic mirrors 4, 5, each reflecting a parallel light beam to the calibrating tube 6 and the measuring tube 7, respectively. The light transmitted through the measuring tube 7 is reflected by the parabolic mirror 19 to the end of the optical fibre 16 which conducts the light to the analysing unit 17 for determining parameters of one or more gaseous substances which are present in the open portion 12 of the measuring tube 7. Light transmitted through the calibrating tube 6 is prevented by the shielding means 20 from reaching the light receiver 15.

When calibration should be carried out for a certain substance, a signal is emitted to the motor 21 which rotates the shielding means 20 to the second position in which light from the measuring tube 5 is prevented from reaching the light receiver 13. Subsequently, zero calibration is effected by supplying zero air or pure nitrogen gas to the calibrating cell 10, and by analysing the light, which is transmitted from the lamp 25 through the calibrating tube 6 and the calibrating cell 10, by the analysing unit and comparing it with the correct zero value of the substance at issue.

Calibration is then carried out for one or more concentrations of the substance at issue. A gas cylinder, which contains a known concentration of the substance, is connected to the gas inlet 11, whereupon the concentration of the gaseous substance in the calibrating cell 10 is determined and compared with the known value. In case of deviations, the amplification is corrected in the analysing equipment.

Calibration can be effected in a corresponding fashion by connecting gas cylinders with known contents to the gas inlet 11 for all gaseous substances that are measured by the equipment. The calibration is fully automatic, while being monitored by the computer.

Figure 2:
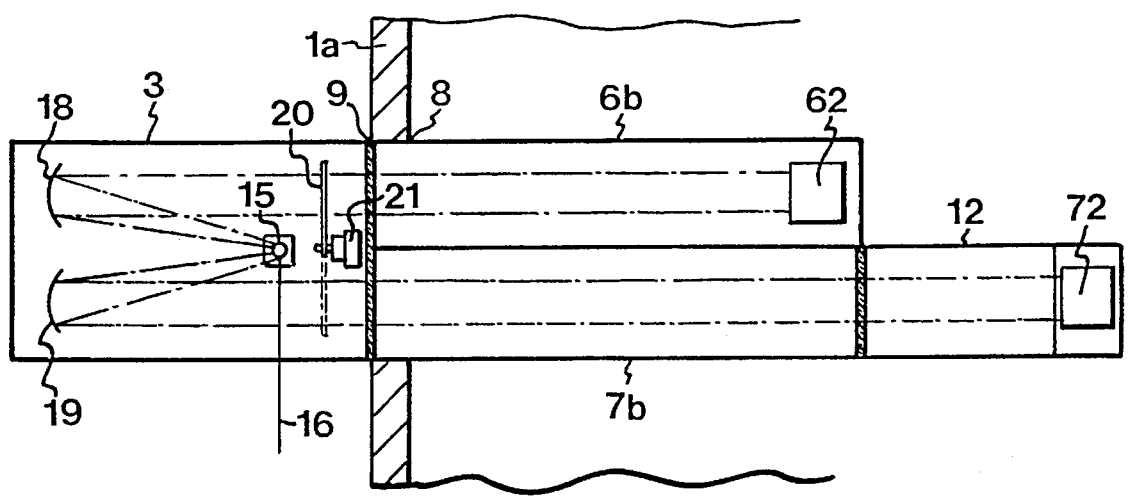
FIG. 2 is a side view of a second embodiment of the equipment according to the invention mounted in a chimney.
Figure 3:
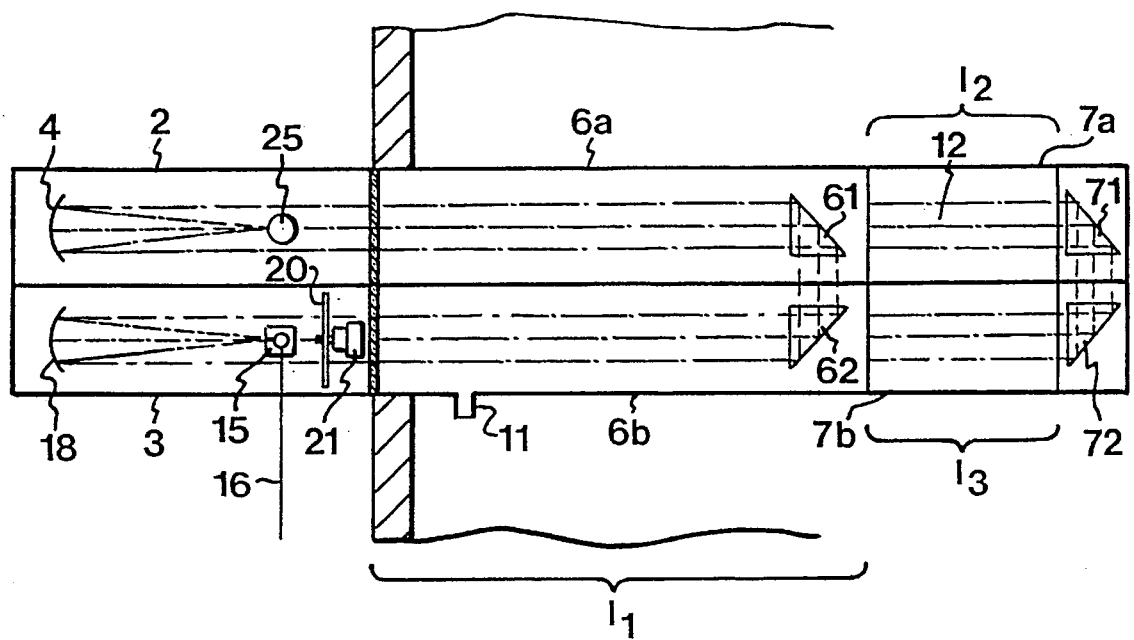
FIG. 3 is a top plan view of the embodiment of the equipment shown in FIG. 2.

FIGS. 2 and 3 illustrate a second embodiment of the equipment according to the invention, mounted in a chimney having a wall 1a. This embodiment is in the first place intended for very large chimneys in which it is difficult or even impossible to mount tubes extending through the entire chimney. As illustrated in FIGS. 2 and 3, the transmitter unit 2 and the receiver unit 3 are placed on the same side of the chimney. The transmitter unit 2 comprises a lamp 25 and two parabolic mirrors 4 (only one shown in FIG. 2) which are arranged to reflect the light form the lamp as two parallel light beams. The receiver unit 3 is positioned adjacent the transmitter unit 2 and contains, as before, a light receiver 15 which is an optical fibre 16 connected to an analysing unit (not shown). The transmitter unit receives two parallel light beams which are reflected to the receiver 15 by means of two parabolic mirrors 18, 19 mounted one below the other.

The equipment according to the invention comprises a calibrating unit 6 which produces a path for the light from the transmitter unit 2 to the receiver unit 3. More specifically, the calibrating unit 6 comprises two parallel tubular members 6a and 6b, as well as two prisms 61 and 62 which are positioned in the far end of the tubular members 6a and 6b relative to the transmitter unit 2 and the receiver unit 3. The prisms 61 and 62 produce a total reflection of the light. The light is thus transmitted through the tubular member 6a and is reflected by the prism 61 to the prism 62 and transmitted through the tubular member 6b to the receiver 15. The calibrating unit 6 has an inlet 11 for calibration gas. Preferably, just one tubular member 6b is used as a calibrating cell 10, the calibrating path being $l_1$.

Under the calibrating unit there is arranged a measuring unit 7 which also comprises two tubular members 7a and 7b, as well as two prisms 71 and 72 which are positioned in the far end relative to the transmitter unit 2 and the receiver unit 3. The measuring unit 7 has an open portion 12 through which the gases in the chimney can flow freely and which forms the measuring path for the measuring operation. In the shown embodiment, the measuring path consists of two partial paths $l_2+l_3$, one between the closed part of the tubular member 7a and the prism 71, and one between the prism 72 and the closed part of the tubular member 7b. The lengths of the tubular members and the open portion are suitably arranged such that the measuring path $l_2+l_3$ and the calibrating path $l_1$ become equally long.

The equipment further comprises a shielding means 20 which is controlled by a motor 21 to take one of two positions.

This embodiment of the equipment functions in the same way as the one described above.

FIG. 4 illustrates a variant of the embodiment shown in FIGS. 2 and 3. In this variant, the calibrating channel is arranged outside the duct. The calibrating channel is positioned in a common transmitter and receiver unit. More specifically, FIG. 4 illustrates a transmitter 2 and a receiver 3 which are juxtaposed in a common casing 40. Like in the embodiments described above, a lamp 25 and two parabolic mirrors 4, 5 are to be found in the transmitter 2. The light from the lamp 25 is divided by the mirrors 4, 5 into a calibrating beam and a measuring beam. Like in the embodiments described above, a light receiver 15 which comprises an optical fibre 16, as well as two parabolic mirrors 18, 19 are to be found in the receiver. In this variant, the light receiver 15 is movable, the optical fibre being rotatable by means of a motor 41 such that it can selectively receive the measuring beam from the mirror 18 or the calibrating beam from the mirror 19. FIG. 4 also shows a part of the measuring unit 7 with the tubular members 7a and 7b which in this case are juxtaposed. As mentioned above, the calibrating unit 6 is arranged in the casing 40 and is thus positioned outside the channel. The calibrating unit 6 comprises two calibrating cells 63, 64 and two prisms 61, 62 for changing the direction of the light. Thus, the calibrating beam is directed from the parabolic mirror 4 through the calibrating cell 63 to the prism 61 which reflects the beam to the prism 62 directing the calibrating beam through the calibrating cell 64 to the parabolic mirror 19 which directs the beam to the light receiver 15. This positioning of the calibrating channel may be advantageous with respect to accessibility and maintenance. Moreover, when mounting the equipment, the duct need be affected but to a small extent. The calibrating cells 63, 64 may further be fitted with controllable heating means 65, thereby making it possible to set the calibrating cells at the same temperature as the gaseous substances in the duct.

The equipment has been described above as mounted in a chimney of course, it can also be used in pipes, conduits and the like.

Many modifications of the described equipment are conceivable. Instead of using a calibrating cell 10 in a part of the calibrating tube 6 as shown in FIG. 1, the entire tube can be used as a calibrating cell. Instead of the calibrating unit and the measuring unit being placed one below the other, as shown in FIGS. 2 and 3, they can be placed side by side. Further the tubular members 6a, 6b and 7a, 7b need not be juxtaposed, but may be spaced apart. The tubular members 6a, 6b and 7a, 7b may then be equally long, and the measuring path may be arranged between the tubular members 7a and 7b. The shielding means may be located either in the transmitter or in the receiver. Instead of being rotatable, the Shield may comprise two shutters which alternatively shield the light from the calibrating unit or the measuring unit. The shielding means may be replaced by a motor which rotates the light transmitter or the light receiver in such a manner that light is transmitted to or received from either the measuring unit or the calibrating unit. The measuring tube 7 and the calibrating tube 6 may have optional cross-sections. Their lengths and diameters may vary, as may also the material of which they are made. The tubes may further be mounted centrally in the duct, for example along a diameter if the duct is of circular cross-section, or non-centrally, for example along a chord if the duct is of circular cross-section.

What I claim and desire to secure by Letters Patent is:

1. Optical analysing equipment for determining parameters of gaseous substances flowing through a duct, comprising:

a fixed light source which is arranged on one side of the duct, a fixed optical arrangement which simultaneously produces, from the light of the light source, a first and a second beam, a light receiver arranged opposite the light source on the other side of the duct, calibrating channel means extending through the duct and including at least one calibrating cell into which a calibrating medium is introducible, the fixed optical arrangement directing the first beam through the calibrating channel means to the light receiver, measuring channel means extending through the duct and arranged to provide a measuring path of a predetermined length in the duct, the fixed optical arrangement directing the second beam through the measuring channel means to the light receiver, light control means by which the light receiver can be caused to selectively receive the first or the second light beam, and gas supply means for supplying the calibrating medium to the calibrating cell.

2. Optical analysing equipment as claimed in claim 1, wherein the light receiver is fixedly arranged, and the light control means includes shielding means.

3. Optical analysing equipment as claimed in claim 1, wherein the light control means includes means for controlling the direction of the light receiver.

4. Optical analysing equipment as claimed in claim 1, wherein the calibrating channel means includes a calibrating tube extending through the duct, the measuring channel means includes a measuring tube which extends through the duct and is open in a portion defining the measuring path, and the calibrating tube and the measuring tube are mounted in parallel and connected with each other.

5. Optical analysing equipment as claimed in claim 1, wherein said gas supply means includes a plurality of gas tanks each storing a different calibrating medium.

6. Optical analysing equipment for determining parameters of gaseous substances flowing through a duct, comprising:

a light source arranged on one side of the duct, an optical arrangement produces, from the light of the light source, a first and a second beam, a light receiver which is arranged on the same side of the duct as the light source, calibrating channel means arranged to define a calibrating channel from the optical arrangement to the light receiver and including at least one calibrating cell into which a calibrating medium is introducible, the optical arrangement directing the first light beam through the calibrating channel means, measuring channel means which is arranged to define a measuring channel from the optical arrangement to the light receiver, which extends a distance into the duct and then back to the light receiver and which has an open portion for providing a measuring path of a predetermined length in the duct, the optical arrangement directing the second light beam through the measuring channel means, light control means by which the light receiver can be caused to selectively receive the first or the second light beam, and gas supply means for supplying the calibrating medium to the calibrating cell.

7. Optical analysing equipment as claimed in claim 6, wherein the measuring channel means includes, two parallel tubular members, each of the two parallel tubular members extending into the duct and having a first end spaced from walls of the duct, and means for changing the direction of the second light beam, which is positioned at said first end of each of the two parallel tubular members.

8. Optical analysing equipment as claimed in claim 7, wherein the second light beam travels along a U-shaped optical path within the measuring channel means.

9. Optical analysing equipment as claimed in claim 6, wherein the calibrating channel means at least partly extend into the duct.

10. Optical analysing equipment as claimed in claim 6, wherein the calibrating channel means is arranged outside the duct and includes controllable heating means for controllably heating said calibrating channel means.

11. Optical analysing equipment as claimed in claim 6, wherein the light source and the optical arrangement are fixedly mounted.

12. Optical analysing equipment as claimed in claim 11, wherein the light control means includes means for controlling the direction of the light receiver.

13. Optical analysing equipment as claimed in claim 11, wherein the light receiver is fixedly mounted, and the light control means includes shielding means for selectively shielding the light receiver from receiving the first or second light beam.

14. Optical analysing equipment as claimed in claim 6, wherein the calibrating channel means includes, two parallel tubular members, each of the two parallel tubular members extending into the duct and having a first end spaced from walls of the duct, and means for changing the direction of the first light beam which is positioned at the first end of each of the two parallel tubular members.

15. Optical analysing equipment as claimed in claim 14, wherein the first light beam travels along a U-shaped optical path within the calibrating channel means.

16. Optical analysing equipment as claimed in claim 14, wherein only one of the two parallel tubular members is used as the calibrating cell.

17. Optical analysing equipment as claimed in claim 6, further comprising a housing arranged on the one side of the duct and housing the light source and light receiver.

18. Optical analysing equipment as claimed in claim 17, wherein the housing further houses the calibrating channel means.

19. Optical analysing equipment as claimed in claim 18, wherein the calibrating channel means includes first and second tubular members.

20. Optical analysing equipment as claimed in claim 19, wherein each of said first and second tubular members includes a calibrating cell.

21. Optical analysing equipment as claimed in claim 20, wherein the first light beam travels along a U-shaped optical path within the calibrating channel means.

22. Optical analysing equipment as claimed in claim 6, wherein said gas supply means includes a plurality of gas tanks each storing a different calibrating medium.

23. Optical analysing equipment for determining parameters of gaseous substances flowing through a duct, comprising:

a fixed light source which is arranged on one side of the duct, a fixed optical arrangement which simultaneously produces, from the light of the light source, a first and second beam, a light receiver arranged opposite the light source on the other side of the duct, calibrating channel means extending through the duct, the fixed optical arrangement directing the first beam through the calibrating channel means to the light receiver, at least one calibrating cell disposed in the calibrating channel means, said calibrating cell being a separate element from said calibrating channel means and receiving a calibrating medium, the first beam passing through said calibrating cell, measuring channel means extending through the duct and arranged to provide a measuring path of a predetermined length in the duct, the fixed optical arrangement directing the second beam through the measuring channel means to the light receiver, and light control means by which the light receiver can be caused to selectively receive the first or the second light beam.

24. Optical analysing equipment as claimed in claim 23, wherein the light receiver is fixedly arranged, and the light control means includes shielding means.

25. Optical analysing equipment as claimed in claim 23, wherein the light control means includes means for controlling the direction of the light receiver.

26. Optical analysing equipment as claimed in claim 23, wherein the calibrating channel means includes a calibrating tube extending through the duct, the measuring channel means includes a measuring tube which extends through the duct and is open in a portion defining the measuring path, and the calibrating tube and the measuring tube are mounted in parallel and connected with each other.

27. Optical analysing equipment as claimed in claim 23, further comprising gas supply means for supplying the calibrating medium to the calibrating cell.

28. Optical analysing equipment for determining parameters of gaseous substances flowing through a duct, comprising:

a light source arranged on one side of the duct, an optical arrangement produces, from the light of the light source, a first and a second beam, a light receiver which is arranged on the same side of the duct as the light source, calibrating channel means arranged to define a calibrating channel from the optical arrangement to the light receiver, the optical arrangement directing the first light beam through the calibrating channel means, said calibrating channel means being arranged outside the duct, at least one calibrating cell disposed in and forming a part of the calibrating channel means, said calibrating cell receiving a calibrating medium, the first beam passing through said calibrating cell, measuring channel means which is arranged to define a measuring channel from the optical arrangement to the light receiver, which extends a distance into the duct and then back to the light receiver and which has an open portion for providing a measuring path of a predetermined length in the duct, the optical arrangement directing the second light beam through the measuring channel means, and light control means by which the light receiver can be caused to selectively receive the first or second light beam.

29. Optical analysing equipment as claimed in claim 28, wherein the measuring channel means includes, two parallel tubular members, each of the two parallel tubular members extending into the duct and having a first end spaced from walls of the duct, and means for changing the direction of the second light beam, which is positioned at said first end of each of the two parallel tubular members.

30. Optical analysing equipment as claimed in claim 29, wherein the second light beam travels along a U-shaped optical path within the measuring channel means.

31. Optical analysing equipment as claimed in claim 28, wherein the calibrating channel means includes controllable heating means for controllably heating said calibrating channel means.

32. Optical analysing equipment as claimed in claim 28, wherein the light control means includes means for moving the light receiver to selectively receive the first or second light beam.

33. Optical analysing equipment as claimed in claim 28, further comprising a housing arranged on the one side of the duct and housing the light source and light receiver.

34. Optical analysing equipment as claimed in claim 33, wherein the housing further houses the calibrating channel means.

35. Optical analysing equipment as claimed in claim 34, wherein the calibrating channel means includes first and second tubular members.

36. Optical analysing equipment as claimed in claim 35, wherein a calibrating cell is disposed in each of said first and second tubular members.

37. Optical analysing equipment as claimed in claim 36, wherein the first light beam travels along a U-shaped optical path within the calibrating channel means.

38. Optical analysing equipment as claimed in claim 28, further comprising gas supply means for supplying the calibrating medium to the calibrating cell.

39. Optical analysing equipment for determining parameters of gaseous substances flowing through a duct, comprising:

a light source arranged on one side of the duct, an optical arrangement produces, from the light of the light source, a first and a second beam, a light receiver which is arranged on the same side of the duct as the light source, calibrating channel means arranged to define a calibrating channel from the optical arrangement to the light receiver, the optical arrangement directing the first light beam through the calibrating channel means, the calibrating channel means including, two parallel tubular members, each of the two parallel tubular members extending into the duct and having a first end spaced from walls of the duct, at least one of said two parallel tubular members forming a calibration cell, and means for changing the direction of the first light beam, the mean for changing being positioned at the first end of each of the two parallel tubular members, measuring channel means which is arranged to define a measuring channel from the optical arrangement to the light receiver, which extends a distance into the duct and then back to the light receiver and which has an open portion for providing a measuring path of a predetermined length in the duct, the optical arrangement directing the second light beam through the measuring channel means, and light control means by which the light receiver can be caused to selectively receive the first or second light beam.

40. Optical analysing equipment as claimed in claim 39, wherein the light source and the optical arrangement are fixedly mounted.

41. Optical analysing equipment as claimed in claim 39, wherein the light receiver is fixedly mounted, and the light control means includes shielding means for selectively shielding the light receiver from receiving the first or second light beam.

42. Optical analysing equipment as claimed in claim 39, wherein the first light beam travels along a U-shaped optical path within the calibrating channel means.

43. Optical analysing equipment as claimed in claim 39, wherein the calibrating cell is only one of the two parallel tubular numbers.

\* \* \* \* \*